(12) United States Patent
Luber et al.

(10) Patent No.: US 6,430,433 B1
(45) Date of Patent: Aug. 6, 2002

(54) APPARATUS FOR IMAGE-SUPPORTED TREATMENT OF A WORK OBJECT

(75) Inventors: Joachim Luber, Essingen; Martin Pelzer, Zang; Michael Kaschke, Oberkochen; Arvids Mackevien, Aalen, all of (DE)

(73) Assignee: Carl-Zeiss-Stiftung (DE)

( * ) Notice: Subject to any disclaimer, the term of this patent is extended or adjusted under 35 U.S.C. 154(b) by 0 days.

(21) Appl. No.: 09/657,348

(22) Filed: Sep. 8, 2000

(30) Foreign Application Priority Data

Sep. 7, 1999 (DE) .......................................... 199 42 591

(51) Int. Cl.⁷ ................................................. A61B 5/05
(52) U.S. Cl. ....................... 600/425; 600/427; 600/429; 345/8
(58) Field of Search ................................. 600/425, 427, 600/429; 345/8

(56) References Cited

U.S. PATENT DOCUMENTS

| 4,722,056 A | 1/1988 | Roberts et al. |
| 4,737,972 A | * 4/1988 | Schoolman |
| 5,383,454 A | 1/1995 | Bucholz |
| 5,855,553 A | * 1/1999 | Tajima et al. |
| 5,920,395 A | 7/1999 | Schulz |
| 5,982,532 A | 11/1999 | Mittlestadt et al. |
| 6,019,724 A | * 2/2000 | Gronningsaeter et al. |

FOREIGN PATENT DOCUMENTS

| EP | 0 501 993 B1 | 11/1990 | ............ G06T/17/00 |
| EP | 0 554 711 B1 | 1/1993 | ............ A61B/19/00 |

* cited by examiner

Primary Examiner—Marvin M. Lateef
Assistant Examiner—Jeoyuh Lin

(57) ABSTRACT

In an apparatus for the image-supported treatment of a work object with a work object data unit and a display unit for the display of work object data from the work object data unit, the display unit makes possible a simultaneous visual sensing, with freedom of head movement, of the instantaneous work object and of the work object data from the work object data unit.

26 Claims, 1 Drawing Sheet

APPARATUS FOR IMAGE-SUPPORTED TREATMENT OF A WORK OBJECT

CROSS-REFERENCES TO RELATED APPLICATIONS

Not applicable.

Statement Regarding Federally Sponsored Research or Development Not applicable.

BACKGROUND OF THE INVENTION

1. Field of the Invention

This invention relates to an apparatus for the image-supported treatment of a work object and more particularly to such an apparatus having a work object data unit, and a display unit for the display of work object data from the work object data unit.

2. Discussion of Relevant Art

Such an apparatus for the image-supported treatment of a work object is known from U.S. Pat. No. 5,383,454 (Bucholz). In this known apparatus, the work object is a patient to be operated on, whose preoperatively prepared diagnostic data, e.g., CT and MRI data, are stored in a work object data unit. During the treatment of the work object, i.e., during the operation, the CT or MRI sectional images are shown on a monitor as work object data, together with a marking which symbolizes a surgical instrument. By means of a position the patient, the position of the marking in the sectional image which can be seen in the monitor then corresponds to the relative position of the surgical instrument and the patient.

U.S. Pat. No. 4,722,056 (Roberts et al.) describes an apparatus of the category concerned, for image-controlled surgery, in which the display unit is an operation microscope. Based on the position sensing unit which senses the relative position of the operation microscope and the patient, the monitor display of a CT sectional image can be reflected into the image field of this operation microscope and superposed, correctly oriented, on the instantaneous image of the patient.

German Patent Application Publication DE 196 40 907 A1 discloses an apparatus of the category concerned for image-supported surgery, with an operation microscope in which sectional images, which match the respective operative situation and are supplemented by preoperatively produced navigation planning data, can be superimposed on the instantaneous image of the patient.

SUMMARY OF THE INVENTION

The invention has as its object to provide an improved apparatus for image-supported treatment of a work object, of the category concerned.

This object is attained by a said display unit that makes possible simultaneous visual sensing, with freedom of head movement, of the instantaneous condition of the work object and of work object data from the work object data unit. Then, by means of such display unit (which makes possible simultaneous visual sensing, with freedom of head movement, of the instantaneous work object and of the work object data from the work object data unit) the person treating the object can move his head substantially freely and nevertheless can always be supplied with the information contained in the work object data unit.

In particular, for the case of application to a surgical operation, the surgeon receives additional information due to the superposition, on the present image of the operation wound, of additional information which can be produced both preoperatively and also intraoperatively; this essential additional information both increases the accuracy of the operation and also offers greater security due to the thereby facilitated additional spatial representation of partially or completely hidden structures.

Thus in advantageous embodiments of the invention, the work object data displayed by the display unit include sectional images, or radiographic or fluoroscopic or C-are images, of the work object or patient.

Furthermore, the work object data displayed by the display unit include an image produced from the work object data and corresponding to an instantaneous surface shape of the work object, whereby the superimposed image can also be perfectly matched to uneven surfaces of the work object.

To further facilitate the treatment of the work object, the work object data displayed by the display unit can include contours of partial structures of the work object, the partial structures being able to lie even beneath the instantaneous surface of the work object.

If the work object data displayed by the display unit are color coded, contrast can be increased and additional information can be displayed in the form of images.

A display of the work object similar to the natural visual impression is attained by a display unit which displays the work object data as stereoscopic images.

In an advantageous embodiment of the invention, the display unit is head-supported, i.e., for example, a so-called "head-mounted display" with transparency, or a unit which writes the work object data directly on the retina of a surgeon by means of a deflectable laser beam. Then if a further position sensing unit senses the relative position of the work object and the head-supported display unit, the work object data can always be formatted, in dependence on the distance and viewing direction of the surgeon, such that the work object data are perfectly matched as regards size and position to the real work object seen through the head-supported display unit or past the head-supported display unit.

A video input or image receiving unit can however also be associated with the display unit, in which case the display unit displays the instantaneous image of the work object supplied by the video input or image receiving unit together with the work object data. In this advantageous embodiment, both the instantaneous image of the work object and also the work object data are produced by auxiliary means. Thereby the instantaneous image of the work object can also be processed, e.g., enlarged. The display unit is then, e.g., a monitor or a flat display screen installed at a convenient viewing height or between the patient and the operator.

In this embodiment, it is important for a positionally correct superposition of the work object and the work object data that a position sensing unit senses the relative position of the video input unit and the work object.

BRIEF DESCRIPTION OF THE DRAWINGS

The invention is explained hereinbelow with reference to preferred embodiments taken together with the accompanying Figures, in which.

DETAILED DESCRIPTION OF THE INVENTION

Figure 1:
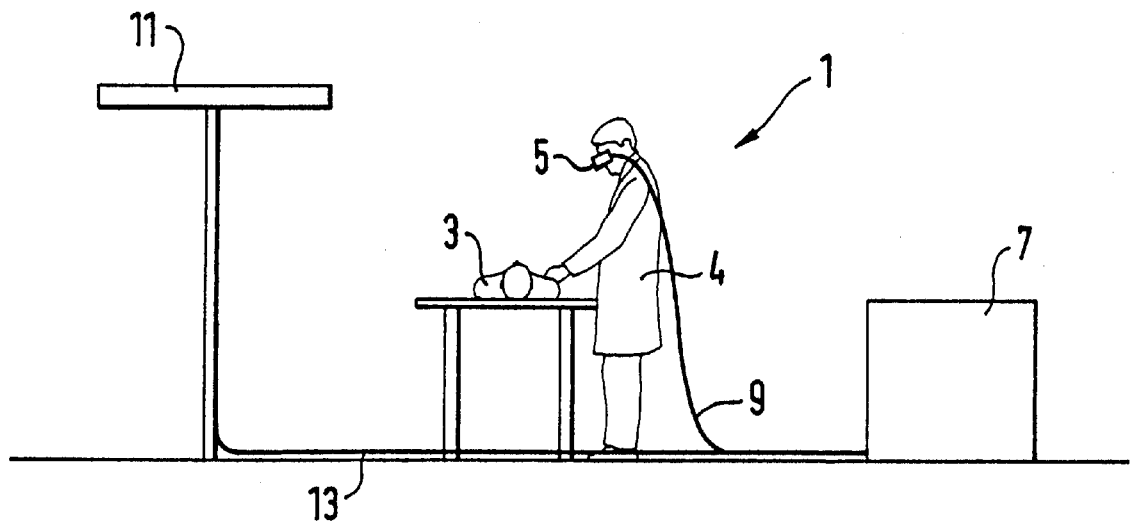
FIG. 1 shows a schematic representation of a first embodiment of the invention.

FIG. 1 shows an apparatus for image-supported treatment of a work object in the example of a surgical operation, in which the work object is a patient 3. Data relating to the patient, particularly image data, are supplied via a data lead 9 from a work object data unit 7 to a display unit, which is constituted as a head-mounted display 5 having transparency and worn by a surgeon 4. A position sensing unit 11 senses the relative position of the patient 3 and the display unit 5. Suitable position sensing units are disclosed, e.g., in U.S. Pat. No. 5,920,395 or in EP 0 501 993 B1, as well as in the previously cited documents.

The sensed position information is supplied via a data lead 13 to the work object data unit 7, and adjusts the display of the patient sectional images, etc., to this relative position.

Figure 2:
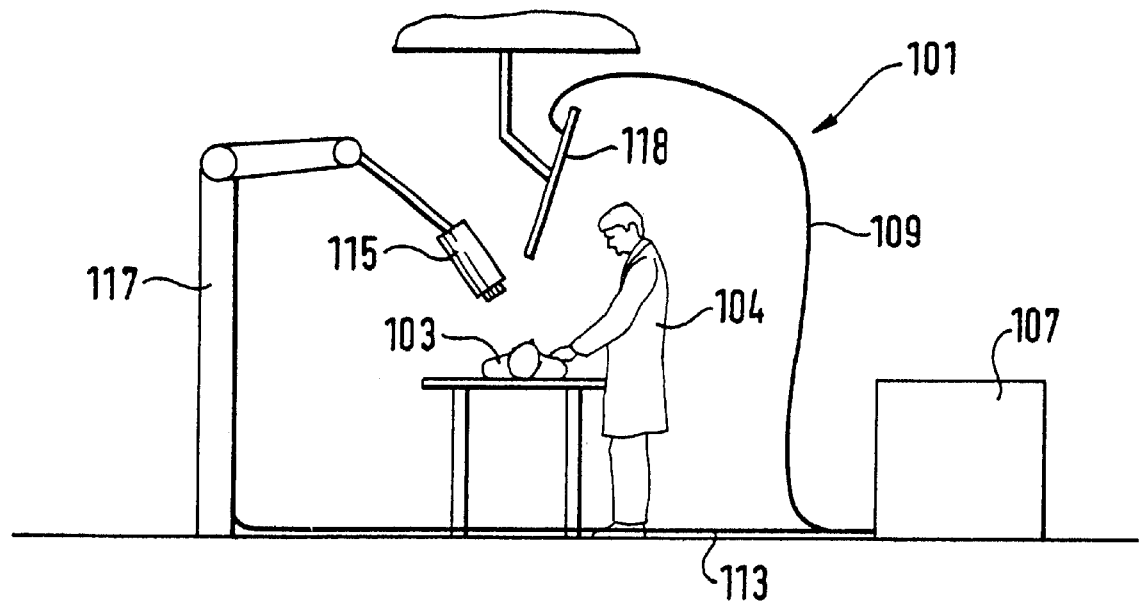
FIG. 2 shows a schematic representation of a second embodiment.

FIG. 2 shows a further apparatus 101 according to the invention, for image-supported surgery. The elements of the apparatus 101 which correspond to the elements in FIG. 1 have the same reference numbers as in FIG. 1 but increased by the number 100.

The apparatus 101 differs from that shown in FIG. 1 in that the display unit is constituted as a ceiling-mounted stereoscopic flat display screen 118, and in that a camera 115 is associated with this display unit and arranged on a jointed stand 117.

The image of the patient 103 taken by the camera 115 is transmitted via a data lead 113 to the work object data unit 107. Together with the image of the patient 103, angle information from the joints of the stand 117 is also transmitted via the data lead 113 for the determination of the relative orientation of the camera 115 and the patient 103. A stand suitable for this purpose is described, e.g., in EP 0 554 711 B1.

What is claimed is:

1. An apparatus for image-supported treatment of a work object, comprising
    a work object data unit, and
    a display unit for the display of work object data from said work object data unit,
    wherein said display unit makes possible simultaneous visual sensing, with freedom of head movement, of an instantaneous condition of said work object and of work object data from said work object data unit, and wherein the display unit allows for a direct view by a user of the work object.

2. The apparatus according to claim 1, wherein work object data displayed by said display unit include sectional images of said work object.

3. The apparatus according to claim 1, wherein work object data displayed by said display unit include radiographic images of said work object.

4. The apparatus according to claim 1, wherein work object data displayed by said display unit comprise fluoroscopic images of a patient to operated on.

5. The apparatus according to claim 1, wherein work object data displayed by said display unit include an image produced from work object data and corresponding to an instantaneous surface shape of said work object.

6. The apparatus according to claim 1, wherein work object data displayed by said display unit include contours of partial structures of said work object.

7. The apparatus according to claim 1, wherein work object data displayed by said display unit are color coded.

8. The apparatus according to claim 1, wherein said display unit displays work object data as stereoscopic images.

9. The apparatus according to claim 1, wherein said display unit comprises a head-supported display unit.

10. The apparatus according to claim 9, further comprising a position sensing unit that senses the relative position of said work object and said head-supported display unit.

11. The apparatus according to claim 1, further comprising an image receiving unit associated with said display unit, wherein said display unit displays an instantaneous image of said work object supplied by said image receiving unit, together with work object data.

12. The apparatus according to claim 11, wherein said instantaneous image of said work object supplied by said image receiving unit is stereoscopic and said display unit displays said instantaneous image of said work object stereoscopically.

13. The apparatus according to claim 10, wherein said position sensing unit senses a relative position of said image receiving unit and said work object.

14. An apparatus for image-supported treatment of a work object, comprising
    a work object data unit, and
    a display unit for the display of work object data from said work object data unit,
    wherein said display unit comprises a head-supported display unit, and
    wherein said display unit makes possible simultaneous visual sensing, with freedom of head movement, of an instantaneous condition of said work object and of work object data from said work object data unit.

15. The apparatus according to claim 14, wherein work object data displayed by said display unit include sectional images of said work object.

16. The apparatus according to claim 14, wherein work object data displayed by said display unit include radiographic images of said work object.

17. The apparatus according to claim 14, wherein work object data displayed by said display unit comprise fluoroscopic images of a patient to operated on.

18. The apparatus according to claim 14, wherein work object data displayed by said display unit include an image produced from work object data and corresponding to an instantaneous surface shape of said work object.

19. The apparatus according to claim 14, wherein work object data displayed by said display unit include contours of partial structures of said work object.

20. The apparatus according to claim 14, wherein work object data displayed by said display unit are color coded.

21. The apparatus according to claim 14, wherein said display unit displays work object data as stereoscopic images.

22. The apparatus according to claim 14, wherein said display unit comprises a head-mounted display unit.

23. The apparatus according to claim 22, further comprising a position sensing unit that senses the relative position of said work object and said head-supported display unit comprises a head-mounted display unit.

24. The apparatus according to claim 14, further comprising an image receiving unit associated with said display unit, wherein said display unit displays an instantaneous image of said work object supplied by said image receiving unit, together with work object data.

25. The apparatus according to claim 24, wherein said instantaneous image of said work object supplied by said image receiving unit is stereoscopic and said display unit displays said instantaneous image of said work object stereoscopically.

26. The apparatus according to claim 23, wherein said position sensing unit senses a relative position of said image receiving unit and said work object.

* * * * *